(12) United States Patent
Lopinti et al.

(10) Patent No.: US 9,611,210 B2
(45) Date of Patent: Apr. 4, 2017

(54) SINGLE-POT SYNTHESIS OF DIALKYL CARBONATES USING CATALYST FROM NATURAL RESOURCE

(71) Applicant: Indian Oil Corporation Limited, Bandra (East), Mumbai (IN)

(72) Inventors: Krishnarao Lopinti, Faridabad (IN); Meeta Sharma, Faridabad (IN); Ashok Kumar Tiwari, Faridabad (IN); Ajay Kumar Arora, Faridabad (IN); Suresh Kumar Puri, Faridabad (IN); Anurag Ateet Gupta, Faridabad (IN)

(73) Assignee: INDIAN OIL CORPORATION LIMITED, Bandra (East) (IN)

( * ) Notice: Subject to any disclaimer, the term of this patent is extended or adjusted under 35 U.S.C. 154(b) by 0 days.

(21) Appl. No.: 15/112,562

(22) PCT Filed: Jan. 12, 2015

(86) PCT No.: PCT/IB2015/050211
§ 371 (c)(1),
(2) Date: Jul. 19, 2016

(87) PCT Pub. No.: WO2015/114474
PCT Pub. Date: Aug. 6, 2015

(65) Prior Publication Data
US 2016/0347702 A1    Dec. 1, 2016

(30) Foreign Application Priority Data
Jan. 30, 2014   (IN) ............................ 336/MUM/2014

(51) Int. Cl.
*C07C 68/04*    (2006.01)
*B01J 21/18*    (2006.01)

(52) U.S. Cl.
CPC ............... *C07C 68/04* (2013.01); *B01J 21/18* (2013.01)

(58) Field of Classification Search
CPC ....................................................... C07C 68/04
See application file for complete search history.

(56) References Cited

U.S. PATENT DOCUMENTS
4,434,105 A    2/1984   Buysch et al.

FOREIGN PATENT DOCUMENTS
CN    1416953    5/2003
CN    101036880    9/2007
CN    102836714 A   *   12/2012

OTHER PUBLICATIONS

Rosenfield et al. Water Environment Research, 2001, 73, 388-393.*
Database CA [Online} Chemical Abstracts Service, Columbus, Ohio, US; Dong Wensheng et al: "Catalyst for preparation of dimethyl carbonate", XP002738069, retrieved from STN Database accession No. 2007:1071939 abstract—& CN 101036880A (Univ Shanxi Normal [CN]) Sep. 19, 2007 (Sep. 19, 2007).
Database CA [Online} Chemical Abstracts Service, Columbus, Ohio, US; Lu Xiaobing et al: "Double-function catalyst for synthesis of cyclic carbonate and dimethyl carbonate", XP002738053, retrieved from STN Database accession No. 2005:648612 abstract—& CN 1416953 (Univ Dalian Science & Eng [CN]) May 14, 2003 (May 14, 2003).
Meeta Sharma et al: "Wood ash as a potential heterogeneous catalyst for biodiesel synthesis", Biomass and Bioenergy, Pergamon, Amsterdam, NL. vol. 41, Feb. 17, 2012 (Feb. 17, 2012), pp. 94-106, XP028406336, ISSN: 0961-9534, DOI: 10.1016/J.BIOBI0E.2012.02.017 [retrieved on Mar. 8, 2012].
PCT/IB/2015/050211 Apr. 16, 2015 International Search Report and Written Opinion.

* cited by examiner

*Primary Examiner* — Matthew Coughlin
(74) *Attorney, Agent, or Firm* — Workman Nydegger

(57) ABSTRACT

The present invention relates to a single-pot method for preparing dialkyl carbonates, the method comprises reaction of alkylene oxide with aliphatic or cyclic aliphatic alcohol, using wood ash catalyst, under $CO_2$ pressure and heating the reaction mixture thereof to obtain dialkyl carbonates.

10 Claims, 2 Drawing Sheets

Figure 1:
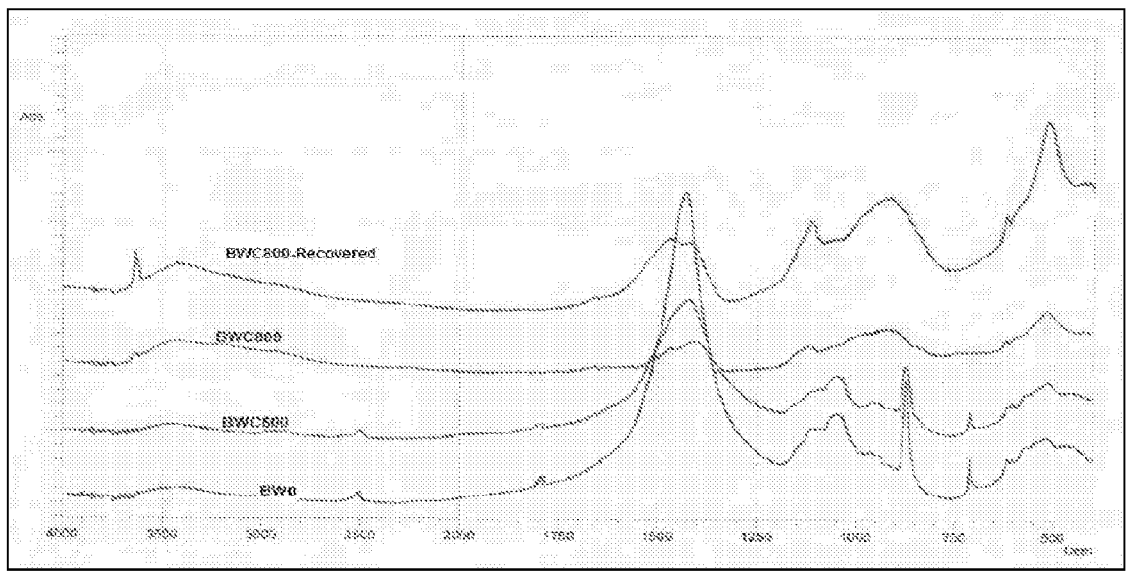

SINGLE-POT SYNTHESIS OF DIALKYL CARBONATES USING CATALYST FROM NATURAL RESOURCE

FIELD OF THE INVENTION

The invention relates to synthesis of dialkyl carbonates from $CO_2$, aliphatic/cyclic aliphatic alcohol and alkylene oxide in presence of renewable catalyst in a single step. Particularly this invention relates to a catalyst prepared directly from biomass used in the synthesis of dialkyl carbonates by single-step preparation.

BACKGROUND OF THE INVENTION $CO_2$ is a major contributor of climate change and worldwide containment of $CO_2$ is a major challenge. In current scenario the challenge for decreasing $CO_2$ in atmosphere needs new ideas and technologies. Generating value added chemicals through green chemistry especially by utilizing greenhouse gas carbon dioxide as raw material is a challenging task. Present fuel oxygenates like ether compounds methyl tert, butyl ether (MTBE), ethyl tert. butyl ether (ETBE), tert. Amyl methyl ether (TAME) and alcohols like methyl alcohol ($CH_3OH$), ethyl alcohol ($C_2H_5OH$) are being used as oxygenates. However, aforementioned oxygenates lead to many problems like corrosiveness, environmental harm, and solubility issues. In order to circumvent these problems dialkyl carbonates are alternate future fuel oxygenates exhibiting attractive environmentally benign nature like non-toxic, non-corrosive and low toxic emissions are being explored.

The dialkyl carbonates especially dimethyl carbonate (DMC), diethyl carbonate (DEC), and ethyl methyl carbonate (EMC) have been widely accepted as fuel oxygenates because of excellent gasoline blending properties like high blending octane numbers, low blending reid vapour pressures (RVP) and lower amounts of toxic emissions compared to ether oxygenates. Several other applications of dialkyl carbonates were explored in green chemical industry for the preparation of polycarbonates, isocyanates, synthetic lubricants, pharmaceutical and agricultural intermediates. In addition, dialkyl carbonates are non-corrosive and highly efficient alkylating agents to replace hazardous phosgene. Due to high volatile value, they are widely used in paint industry.

Scientists have developed several processes for the synthesis of dialkyl carbonates. The conventional process involves usage of hazardous chemicals like phosgene or carbon monoxide as starting materials. The alternative and non-hazardous process involve utilization of $CO_2$ as raw material, which is eco-friendly and cost-effective process.

The eco-friendly synthetic route involves reaction of carbon dioxide with alcohol to generate corresponding dialkyl carbonates. Amongst dialkyl carbonates, dimethyl carbonate and diethyl carbonate synthesis has been well recognised and explored. In prior art literature, number of homogeneous catalysts (e.g. tin complexes: distannoxanes) and heterogeneous catalysts (e.g. $CeO_2$, modified Zirconia, Zeolites) have been investigated and have shown limitations of poor conversions either due to the thermodynamic limitation of reaction or due to catalyst deactivation.

Therefore, finding an alternate route for the synthesis of DMC and DEC from $CO_2$ involving in situ transesterification of cyclic carbonate (synthesised from epoxide and $CO_2$) with alcohol in presence of suitable catalyst would be well attempted. Significant efforts have already been devoted in efficient catalyst development for DMC & DEC synthesis from cyclic carbonates. The synthesis of DMC and DEC from epoxide through two step mechanism involving synthesis of cyclic carbonate in $1^{st}$ step and then transesterifying to DMC and DEC is not economical for commercialisation.

Keeping in view the limitation associated with above processes, one-pot synthesis of DMC/DEC from $CO_2$, alkylene oxide and alcohol was explored to make the process more viable, eco-friendly and cost-effective. Single-pot synthesis of DMC/DEC from $CO_2$, alkylene oxide and alcohol in presence of several catalysts mainly metal oxides, inorganic bases/metal oxides, inorganic bases/phosphonium halide on polyethylene glycol, TBAB/$Et_3N$, ionic liquid, KOH/4A° MS, biomettalic Cu—Ni/4A° MS, anion exchange resins, and Mg/Smacilite etc. have been reported in the literature.

The process conditions in single step synthesis of DEC and DMC from propylene oxide in literature references are reported to involve low catalytic activity, formation of side products, difficulty in catalyst separation and recyclability, and requirement of costly raw materials to synthesise the above catalysts.

Several patents have been published on synthesis of dialkyl carbonates from transesterification of cyclic carbonates with appropriate alcohol in presence of both homogeneous and heterogeneous catalysts. Few publications have been found on direct synthesis of dialkyl carbonates from alkylene oxide, $CO_2$ and alcohol in single-pot reaction.

Single-pot synthesis of dialkyl carbonates is reported in U.S. Pat. No. 4,434,105 (EP 000777), which reveals the synthesis of dialkyl carbonates namely dimethyl carbonate and diethyl carbonate from ethylene oxide/propylene oxide, methanol/ethanol and carbon dioxide in the presence of homogeneous as well heterogeneous catalysts in single pot reaction. Dialkyl carbonates mainly DMC and DEC were prepared in the presence of catalysts NaI/$Tl_2CO_3$, NaI/TlOH, NaI, $Tl_2CO_3$, Imidazole, TBAB, TEAB and organic bases like guanidine, DABCO, triethanol amine and etc. Yields of DMC and DEC are high with ethylene oxide compared to propylene oxide, which may be due to sterically more feasible product formation. The main drawback of this work is expensive catalysts and halogen containing catalysts.

U.S. Pat. No. 5,218,135 has revealed two step synthesis of dialkyl carbonate from $CO_2$, alkylene oxide and alcohol in presence of bifunctional catalysts. Initially cyclic carbonate was prepared from alkylene oxide and $CO_2$ in presence of bifunctional catalysts then cyclic carbonate was treated with alcohol in presence of bifunctional catalyst to yield corresponding dialkyl carbonate.

Recently US 2013/0267727 A1 and also US 2006/7084292 B2 have explored the feasibility of integrated process for production of dialkyl carbonates and diols from alkylene oxide, carbon dioxide and aliphatic alcohol. In this integrated process, initially alkylene oxide was reacted with carbon dioxide to produce crude cyclic carbonate in the presence of homogeneous catalyst. Second step involve reaction between crude cyclic carbonate and alcohol in the presence of heterogeneous catalysts like metal oxides to produce dialkyl carbonates.

U.S. Pat. No. 5,218,135, U.S. Pat. No. 7,491,837 B2 and WO 03/000641 A1 also described the integrated process of making dialkyl carbonates for alkyl alcohol, carbon dioxide and alkylene oxide. They initially prepared cyclic carbonate from alkylene oxide and carbon dioxide in presence of homogeneous catalyst. In second process cyclic carbonate reacts with alcohol for producing dialkyl carbonate in the presence of transesterification catalyst.

The catalysts used in the prior art are expensive, non-renewable and non-recyclable. Formation of by-product $H_2O$ during reaction deactivates the catalyst for further use. Also low product yields are reported in references of prior art.

In prior art literature, heterogeneous catalysed single pot synthesis of dialkyl carbonates from propylene oxide, $CO_2$ and methanol in presence of Mg-Smectite gave 32.30% of dimethyl carbonate (Green chemistry, 2003, 5, 71-75).

Present invention discloses a preparation methodology of dialkyl carbonates using wood ash catalyst; involving insertion of $CO_2$ molecule in to an alkylene oxide and transesterification of that intermediate compound with aliphatic alcohol in to dialkyl carbonate in single pot reaction. The inherent property of wood ash catalyst of $CO_2$ insertion along with the property of transesterification was explored for the synthesis of dialkyl carbonates.

The present invention addresses one or more such problems of the prior art as discussed above. However, it is contemplated that the invention may prove useful in addressing other problems also in a number of technical areas.

SUMMARY OF THE INVENTION

The present invention relates to a single-pot method for preparing dialkyl carbonate, the method comprising dissolving an alkylene oxide in an aliphatic or cyclic aliphatic alcohol, adding a wood ash catalyst, adding $CO_2$ gas under pressure and heating the reaction mixture, cooling the reaction mixture to about room temperature, and depressurizing to obtain dialkyl carbonate. The reaction mixture is filtered to recover the catalyst. The aliphatic or cyclic aliphatic alcohols are $C_1$ to $C_{12}$ aliphatic alcohols and $C_1$ to $C_{12}$ cyclic aliphatic alcohols. The aliphatic or cyclic aliphatic alcohol is selected from methanol, ethanol, propanol, butanol, amyl alcohol, hexanol, octanol, cyclohexanol and octahexanol. The alkylene oxide is selected from the group comprising ethylene oxide, propylene oxide, 1,2-epoxy butane, 1,2-epoxy pentane and 1,2-epoxy hexane. The pressure is about 70-90 bar. The heating is carried out at a temperature range of about 100-180° C. The filtered catalyst is washed with an aliphatic alcohol and dried at about 120° C. for 24 hours for reuse. The aliphatic alcohol is methanol or ethanol. The catalyst obtained is reused in the process of claim 1.

The present invention also relates to a method of preparing wood ash catalyst comprising washing wood with deionized water; drying the wood until the wood attains constant weight; dry ashing the wood; and calcining the wood to obtain wood ash catalyst.

The wood is selected from *Azadirachta indica* and *Acacia nilotica*. The wood is dried at a temperature of about 60° to 80° C. The dry ashing is carried out at a temperature of 525±25° C. The calcining is carried out at a temperature of about 300° C. to about 1200° C.

Our invention presents the wood ash catalyst $BWC_{800}$ as heterogeneous catalyst for the synthesis of dimethyl carbonate from propylene oxide, $CO_2$ and methanol with good yield of 51.11% which is better than reported in literature. Activity of wood ash catalyst $BWC_{800}$ was also further evaluated with several alcohols for the synthesis of respective dialkyl carbonates. Amongst, diethyl carbonate was synthesised from propylene oxide, $CO_2$ and ethanol with highest yield of 53.43%.

The following terms are defined as follows:

$BW_0$: Wood ash without calcination. On using $BW_0$ as catalyst for the preparation of dialkyl carbonates, the overall yield is 6-7%. The reason for the low yield of dialkyl carbonetes is that wood ash contains primarily carbonates of Ca, Mg along with other metal components and less basic in nature. It also does not contain sintered calcium silica phosphate compound. So, the dialkyl carbonate yield is very less in the reaction with $BW_0$.

$BWC_{500}$: Wood ash calcined at temperature 500° C. On using $BWC_{500}$ as catalyst for the preparation of dialkyl carbonates, the overall yield is 42.46%. The reason for the moderate yield is the partial conversion into active catalyst such as some amount of calcium oxide (CaO) and magnesium oxide (MgO) along with small amount of calcium silica phosphates were observed in XRD studies. Accordingly conversion to dialkyl carbonate is not complete and moderate.

$BWC_{800}$: Wood ash calcined at temperature 800° C. On using $BWC_{800}$ as catalyst for the preparation of dialkyl carbonates, the overall yield is 53.43%. The reason for the high yield is that catalyst from wood ash at 800° C. contains completely converted magnesium oxide (MgO) and calcium oxide (CaO) along with sintered calcium silica phosphates which gave highest dialkyl carbonate yield.

BRIEF DESCRIPTION OF ACCOMPANYING DRAWINGS

Figure 2:
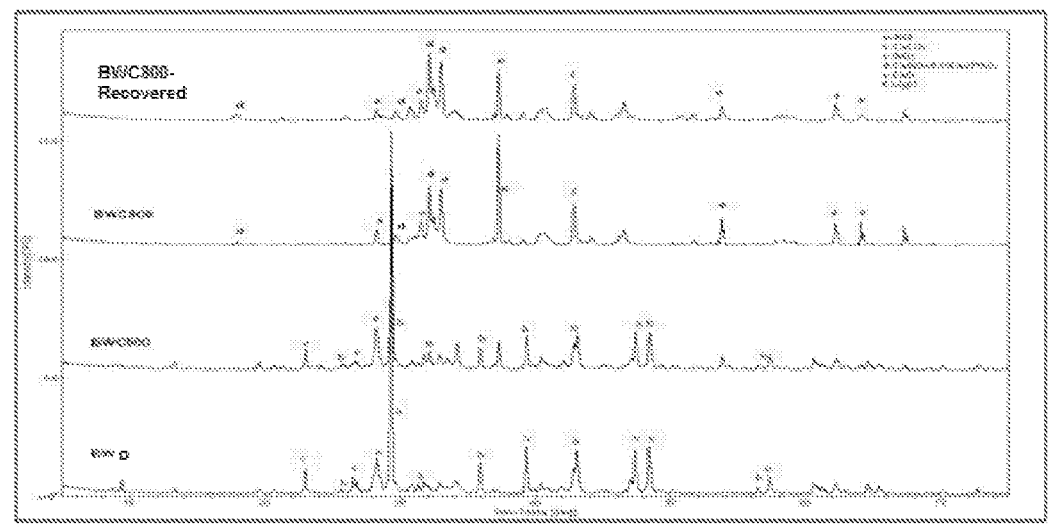

FIG. 1: IR spectrum of wood ash catalysts;
FIG. 2: XRD spectrum of wood ash catalysts; and
FIG. 3: TGA analysis of $BWC_{800}$ wood ash catalyst.

DETAILED DESCRIPTION OF THE INVENTION

The present invention discloses a preparation methodology of dialkyl carbonates (fuel oxygenates) by reacting $CO_2$, aliphatic/cyclic aliphatic alcohol and alkylene oxide in presence of renewable catalyst in a single step, the said catalyst being prepared from biomass.

An aspect of the invention discloses the preparation methodology of the catalyst; said catalyst being prepared directly from the biomass. Another aspect of the present invention is the use of the novel renewable catalyst prepared from biomass in a single step reaction to produce dialkyl carbonates from aliphatic & cyclic alcohols and propylene oxide by utilizing $CO_2$.

An aspect of the present invention is that the catalyst prepared from wood ash is novel, economical and eco-friendly. The wood ash used in accordance with this invention can be obtained from biomass, including but not necessarily limited to, wood of trees such as *Azadirachta indica, Acacia nilotica*. Another aspect of the invention discloses the production of alkylene glycol as by-product during synthesis of dialkyl carbonates in presence of renewable catalyst.

The wood ash catalyst is basic in nature. Composition of wood ash catalyst is mixture of oxides of Ca and Mg along with sintered material calcium silica phosphates. Wood ash also contains potassium and small quantities of other metal derivatives. The typical combination of all these compounds in wood ash catalyst makes it a suitable catalyst for various organic transformations. We explored the inherent properties of wood ash catalyst and utilized for the single pot synthesis of dialkyl carbonates from $CO_2$, alkylene oxide and alcohol. The wood ash catalyst catalyses $CO_2$ insertion in to alkylene oxide to form cyclic carbonate which is further converted in situ to dialkyl carbonates in the presence of alcohols. Therefore, wood ash catalyst helps to convert $CO_2$ to dialkyl carbonates in the presence of alcohols in a single pot reaction conditions in comparison to prior art claim of dialkyl carbonates synthesis from $CO_2$ mostly carried out in two separate steps by using two different types of catalysts. The advantage of this invention is wood ash catalyst able to perform synthesis of dialkyl carbonates from $CO_2$ in a single pot reaction conditions.

The preparation methodology according to the present invention involves washing the wood with deionised water and then drying until the wood attains constant weight. The wood was dry ashed separately and calcined. One-pot synthesis of dialkyl carbonates from aliphatic/cyclic aliphatic alcohol, $CO_2$ and alkylene oxide was carried out in a controlled heating system.

In a preferred embodiment, the preparation of dialkyl carbonate involves washing the wood with deionised water and then drying at about 60°-80° C. until the wood attains constant weight. The wood was dry ashed separately and calcined, at temperature ranges of about 300° C. to about 1200° C. One-pot synthesis of dialkyl carbonates from aliphatic/cyclic aliphatic alcohol, $CO_2$ and alkylene oxide was carried out in an autoclave vessel fixed to stirrer and controlled heating system. In drying step, the wood is heated at a temperature range of 60 to 80° C. for 24 hours to remove moisture and impurities present in the wood after washing with deionised water. In the dry ashing step, the wood is burned in a furnace at 525° C.±25° C. (Ref. TAPPI, Ash in wood, pulp, paper and paperboard: combustion at 525° C., T211 om-93, 1993).

The aliphatic alcohols/cyclic alcohols used according to the present invention include $C_1$ to $C_{12}$ aliphatic alcohols, $C_1$ to $C_{12}$ cyclic aliphatic alcohols like cyclic pentanol, cyclic hexanol, more preferably methanol, ethanol, propanol, butanol, amyl alcohol, hexanol, ocyanol, cyclohexanol, octahexanol. The alkylene oxides used according to the present invention include ethylene oxide, propylene oxide, 1,2-epoxy butane, 1,2-epoxy pentane, 1,2-epoxy hexane.

The single-pot method for preparing dialkyl carbonate comprises dissolving alkylene oxide in an aliphatic/cyclic aliphatic alcohol, adding wood ash catalyst, adding $CO_2$ gas at a workable pressure range and heating the reaction mixture, cooling the reaction mixture to about room temperature, and depressurizing to obtain dialkyl carbonate. The reaction mixture is filtered to remove the catalyst. The filtered catalyst was washed with an aliphatic alcohol, preferably methanol or ethanol and dried for reuse.

In a preferred embodiment, the single-pot method for preparing dialkyl carbonate comprises dissolving alkylene oxide in an aliphatic/cyclic aliphatic alcohol, adding wood ash catalyst in the autoclave vessel. The autoclave vessel was pressurised with $CO_2$ gas. At the workable pressure range of about 70-90 bar and temperature range of about 100-180° C., the reaction mixture was stirred constantly for about 24 hours. Then reaction mixture was cooled to room temperature, depressurised and filtered to remove the catalyst. The filtered catalyst was washed with an aliphatic alcohol, preferably methanol or ethanol and dried at about 120° C. for about 24 hours for reuse. The identification and quantification of the components in the reaction mixtures were performed with GC and GC-MS analysis.

Catalyst prepared from wood ash is novel, economical and eco-friendly compared to catalysts reported in literature for the synthesis of dialkyl carbonates. The developed process methodology is single step reaction to produce dialkyl carbonates from aliphatic/cyclic alcohols and propylene oxide by utilizing $CO_2$. Separation and regeneration of catalyst is performed by low cost techniques.

The $CO_2$ insertion reaction into propylene oxide requires activation of epoxide and activation of $CO_2$, which is the most crucial step. This is pull-push of electrons of both the molecules by two different categories of metals. Wood ash catalyst has combination of the above properties due to presence of metal oxides, mixed metal oxides along with alkali earth metal halides. Both alcohol and $CO_2$ are equally capable to insert into epoxide ring but catalyst should be selective for $CO_2$ insertion. Wood ash catalyst showed typical interaction with $CO_2$ and activated it successfully towards epoxide insertion reaction. Prior art literature shows that oxides of Ca and Mg can perform transesterification reactions of propylene carbonate with alcohols (*Indian Journal of chemistry*, 52A, 459-466, 2013). Wood ash catalyst able to perform both $CO_2$ insertion and transesterification reactions simultaneously with high selectivity.

The prepared catalysts were evaluated for their alkalinity (pH), particle size and surface area, results are shown in Table 1. The alkalinity of $BW_0$ (wood ash without calcination), $BWC_{500}$ (wood ash calcined at 500° C.) and $BWC_{800}$ (wood ash calcined at 800° C.) catalysts were found to be 11.28, 11.68 and 12.02 respectively. It was observed that the calcination temperature affects the alkalinity of the catalysts. The results showed that $BWC_{800}$ catalyst calcined at 800° C. temperatures has highest alkalinity may be due to thermal decomposition of $CaCO_3$ to CaO which is having higher soluble alkalinity. This observation is in line with that reported in literature, which indicates the increase of alkalinity with the increase of calcination temperature [Biomass and Bioenergy 41 (2012) 94-106]. Further, recovered $BWC_{800}$ catalyst alkalinity was determined as 12.04 in order to check the stability of active basic sites present on the catalyst. In addition, XRD pattern of recovered catalyst also confirms the stable catalyst structure after the reaction (FIG. 2).

TABLE 1

Alkalinity, surface area and particles size of the wood ash catalysts

| Catalyst | Alkalinity (at 28.0° C.) | SA ($m^2$/gm) | APS (μm) |
| --- | --- | --- | --- |
| $BW_0$ | 11.28 | 2 | 20.76 |
| $BWC_{500}$ | 11.688 | 1.6 | 25.65 |
| $BWC_{800}$ | 12.025 | <1 | 36.26 |
| $BWC_{800}$ (Recovered) | 12.048 | 8 | 56.77 |

As seen from the Table 1, the surface area of wood ash catalysts decreases with increase of calcination temperature. The surface areas of $BW_0$, $BWC_{500}$ and $BWC_{800}$ catalysts were 2.0, 1.6 and <1 $m^2$/gm respectively. Lower surface area of $BWC_{800}$ catalyst than $BWC_{500}$ catalyst is due to conversion of $CaCO_3$ into CaO which results in sintering by the formation of calcium phosphate silicate. The observation was further confirmed by XRD study of the catalyst structure (FIG. 2).

The particle sizes of $BW_0$, $BWC_{500}$ and $BWC_{800}$ were determined as 20.76, 25.65 and 36.26 μm respectively. The result reveals that particle size of the catalysts has increased with increasing calcination temperature [Biomass Bioenergy 4 (1993) 103-106]. The possible reason may be the increase of sintering with increase of temperature, leads to increase in particle size as reported in earlier study [Biomass and Bioenergy 41 (2012) 94-106]. Recovered $BWC_{800}$ catalyst particle size is 56.77 μm may be due to the formation of some amounts of calcium hydroxide and carbonates however this does not has any effect on catalyst performance on subsequent reuse. These results were further supported by XRD analysis as shown in FIG. 2.

IR Analysis

The FTIR spectra of wood ash catalysts are given in FIG. 1. The spectra of $BW_0$ catalyst shows the presence of carbonates, $CO_3^{-2}$ (the peaks at 1795, 1427, 875 and 711 $cm^{-1}$) and phosphates, $PO_4^{-3}$ components (peaks at 1112, 1047 and 617 $cm^{-1}$), confirms the presence of metal carbonates (mainly $CaCO_3$) and metal phosphates. The IR spectrum of $BWC_{500}$ catalyst shows similar spectral features. After calcination at 800° C., $BWC_{800}$ catalyst indicates the presence of metal oxides (peak at 3425, 2960, 1462, 1408, 921 and 516 $cm^{-1}$) along with the calcium phosphates silicate (peak at 2856, 1388 and 1118 $cm^{-1}$). The results reveal that the calcination at higher temperature results in carbonates decomposition to metal oxides.

IR analysis of recovered $BWC_{800}$ catalyst reveals that structure of the catalyst is remain same after reaction however formation of very small quantity of calcium hydroxide (3645 $cm^{-1}$) was observed.

XRD Analysis

The XRD pattern of $BW_0$, $BWC_{500}$, $BWC_{800}$ and recovered $BWC_{800}$ catalyst is shown in FIG. 2. The results indicate that $BW_0$ catalyst is mainly composed of $CaCO_3$ along with small amount of KCl and $SiO_2$. After calcination at 500° C., the pattern of crystalline phases remains same in $BWC_{500}$ catalyst with additional appearance of CaO crystalline phase.

On further calcination at 800° C., $BWC_{800}$ catalyst shows the presence of metal oxides mainly CaO and MgO along with KCl and mixed metal phosphates $Ca_2SiO_4 \cdot 0.05Ca_3(PO_4)_2$. These results were further confirmed by elemental analysis.

XRD analysis of recovered $BWC_{800}$ catalyst show same structure as of fresh $BWC_{800}$ catalyst. However some decreasing intensity of crystalline phases of CaO, MgO and mixed metal phosphates is due to formation of calcium hydroxide is confirmed by increasing of pH value and IR analysis.

Elemental Analysis

The elemental analysis of $BWC_{800}$ catalyst shows the presence of Ca, K and Mg in higher amounts as 32.30, 10.91 and 5.79 mass fraction percentage respectively. While the Na, P and Al are in notable amounts as 1.42, 1.40 and 1.90 mass fraction percentage respectively, the transition metals present in $BWC_{800}$ are mainly Fe, Mn and Zn in trace quantities. The presence of the minor quantities of Silicon was also confirmed by XRF analysis.

TGA Analysis

In heterogeneous catalysts, stability of active sites on catalyst surface is very important. $BWC_{800}$ catalyst stability was measured by TG analysis carried out on TG model 2950 Hi Resolution modulated TGA, with heating rates 10° C./min, temperature ramp up to 800° C.

Figure 3:
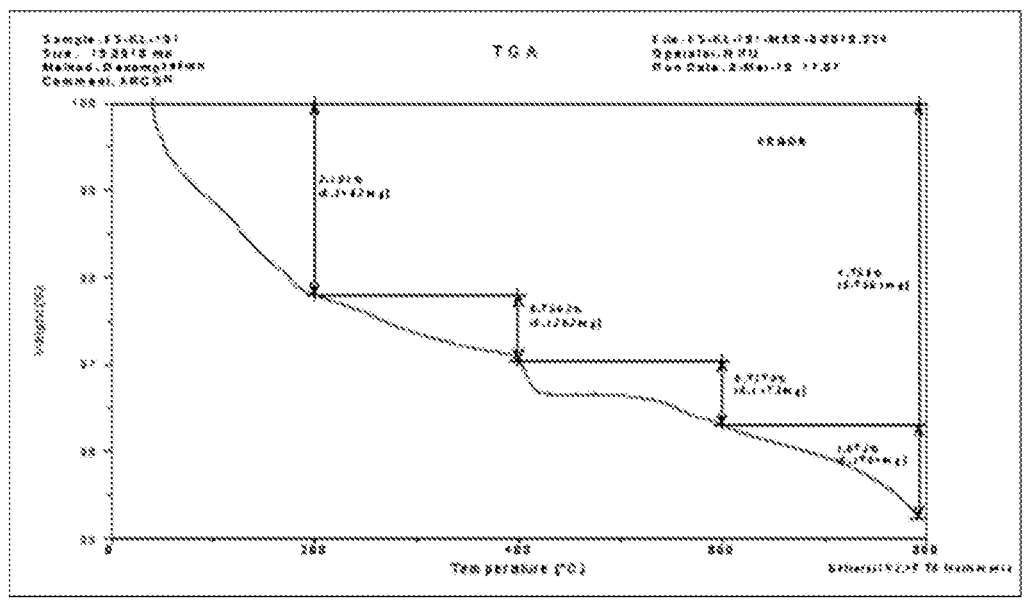

The results given in the FIG. 3 shows the weight loss of 2.19 wt. % is observed at 198° C. corresponding to the removal of loosely absorbed water on the surface of catalyst. Further the decomposition of calcium carbonate at 425° C. and 660° C. producing calcium oxide associated with 1.809 wt. % weight loss. Additionally, the stability of $BWC_{800}$ catalyst is confirmed by metal analysis of carbonate product produced with XRF technique and found all the metal <1 mg/Kg. Above findings also confirm the non-leaching behaviour of the catalyst and are in agreement with the earlier study [Biomass and Bioenergy 41 (2012) 94-106].

These dialkyl carbonates are extensively studied as fuel oxygenates in the literature (Energy & Fuels 1997, 11, 2-29). The octane number, RVP and toxic emissions from dialkyl carbonates are compared with ether oxygenates and reported in the literature (Energy Fuels 2010, 24, 4812-4819). However, synthesis of these dialkyl carbonates reported through phosgene route which is corrosive and environmentally not favourable. We have developed environmentally safe method for preparation of dialkyl carbonates from $CO_2$ as feed stock and carrying out the preparation in single pot in presence of wood ash as novel catalyst.

The octane number of prepared dialkyl carbonates viz. DMC, DEC blend with gasoline is studied by CFR (Combustion Fuel Research)* engine test method, the results are as follows in Table 2:

TABLE 2

| S. No: | FUEL TYPE | RON by CFR engine test ASTM D2699 | Improved RON value | RVP values (KPa) |
|---|---|---|---|---|
| 1. | Gasoline BSIV | 92.2 | NA | 48.6 |
| 2. | 100% DMC | 111 | NA | 11.1 |
| 3. | 100% DEC | 114 | NA | 6.3 |
| 2. | 6% DMC in BSIV gasoline | 93.4 | 1.2 | 48.0 |
| 3. | 8% DEC in BSIV gasoline | 94.2 | 2.0 | 46.1 |

Blending carried out to keep overall oxygen content in gasoline to 2.7% by mass as per IS 2796-2008 motor gasoline BS IV specifications.

These dialkyl carbonates are extensively studied as fuel oxygenates in the literature (Energy & Fuels 1997, 11, 2-29). The octane number, RVP and toxic emissions from dialkyl carbonates were compared with ether oxygenates and reported in the literature (Energy Fuels 2010, 24, 4812-4819). The synthesis of these dialkyl carbonates through phosgene route is corrosive and environmentally not favourable. We have developed environmentally safe method from $CO_2$ as feed stock and single pot reaction in presence of wood ash as catalyst. Having described the basic aspects of the present invention, the following non-limiting examples illustrate specific embodiment thereof.

EXAMPLES

Example 1

One-Pot Synthesis of DEC from Ethanol, $CO_2$ and Propylene Oxide Using $BW_0$ as Catalyst In a 700 ml autoclave, propylene oxide (10.17 gm, 0.175 mol), ethanol (64.70 gm, 1.40 mol) and wood ash catalyst $BW_0$ (7.0 gm, 10% wt/wt) were charged. The autoclave vessel was pressurised with $CO_2$ pressure, heated to reach 150° C. temperature and 80 bar pressure under constant stirring for reaction time 24 hours. Then reaction mixture was cooled to room temperature, depressurised and filtered to remove the catalyst. The filtered catalysts was washed with ethyl alcohol and dried at 120° C. for 24 hours before reuse. The reaction mixture was subjected to distillation. First fraction contains mixture of excess ethanol and DEC and second fraction contains mixture of propylene glycol and propylene carbonate. The identification and quantification of the components in the fractions were performed with GC and GC-MS analysis.

Analytical analysis of ethanol fraction reveals that formation of DEC is 1.26 gm (2.20 mmol). The calculated yield of DEC corresponding to propylene oxide is 6.06%.

Example 1 explains that reaction mixture was cooled to room temperature after 24 hours, depressurised and filtered to remove the catalyst. The filtered catalyst was washed with methanol (20 ml) dried at 120° C. for 24 hours for reuse.

Example 2

Synthesis of DEC from Ethanol, $CO_2$ and Propylene Oxide Using $BWC_{500}$ as Catalyst Propylene oxide (10.17 gm, 0.175 mol), ethanol (64.70 gm, 1.40 mol) and wood ash catalyst $BWC_{500}$ (7.0 gm, 10% wt/wt) were charged into 700 ml autoclave vessel. The autoclave vessel was pressurised with $CO_2$ pressure, heated to 150° C. temperature and 80 bar pressure under constant stirring during the reaction for 24 hours. Reaction mixture work up was carried out as described in example 1.

The quantitative analysis of ethanol fraction reveals that formation of DEC is 8.79 gm (74.47 mmol). The calculated yield of DEC with respect to propylene oxide is 42.46%.

Example 3

Synthesis of DEC from Ethanol, $CO_2$ and Propylene Oxide Using 10 wt % $BWC_{800}$ as Catalyst 700 ml autoclave was charged with propylene oxide (10.17 gm, 0.175 mol), ethanol (64.70 gm, 1.40 mol) and wood ash catalyst $BWC_{800}$ (7.0 gm, 10% wt/wt). The autoclave vessel was pressurised with $CO_2$ pressure, heated to reach 150° C. temperature and 80 bar pressure under constant stirring during the reaction for 24 hours. Then reaction mixture was cooled to room temperature, depressurised and filtered to remove the catalyst. The filtered catalysts was washed with ethyl alcohol and dried at 120° C. for 24 hours before reuse. The reaction mixture was subjected to distillation. First fraction contains mixture of excess ethanol and DEC and second fraction contains mixture of propylene glycol and propylene carbonate. The identification and quantification of the components in the fractions were performed with GC and GC-MS analysis.

The quantitative analysis of ethanol fraction reveals that formation of DEC is 11.06 gm (93.67 mmol). The calculated yield of DEC from propylene oxide is measured as 53.43%.

Example 4

Synthesis of DEC from Ethanol, $CO_2$ and Propylene Oxide Using $BWC_{800}$ as Catalyst at 70 Bar $CO_2$ Pressure In a 700 ml autoclave, propylene oxide (10.17 gm, 0.175 mol), ethanol (64.70 gm, 1.40 mol) and wood ash catalyst $BWC_{800}$ (7.0 gm, 10% wt/wt) was charged. The autoclave vessel was pressurised with $CO_2$ pressure, heated to 150° C. temperature and 70 bar pressure under constant stirring for reaction time 24 hours. Reaction mixture work up was carried out as described in example 3.

The analytical analysis of ethanol fraction reveals the formation of DEC is 10.23 gm (86.65 mmol). The calculated yield of DEC corresponding to propylene oxide is 49.42%.

Example 5

Synthesis of DEC from Ethanol, $CO_2$ and Propylene Oxide Using $BWC_{800}$ as Catalyst at 90 Bar $CO_2$ Pressure Propylene oxide (10.17 gm, 0.175 mol), ethanol (64.70 gm, 1.40 mol) and wood ash catalyst $BWC_{800}$ (7.0 gm, 10% wt/wt) were charged in to 700 ml autoclave vessel. The autoclave vessel was pressurised with $CO_2$ pressure, heated to reach 150° C. temperature and 90 bar pressure under constant stirring during the reaction for 24 hours. Reaction mixture work up was carried out as described in example 3.

Analytical analysis of ethanol fraction reveals that formation of DEC is 8.78 gm (74.38 mmol). The measured yield of DEC from propylene oxide is 42.41%.

Example 6

Synthesis of DEC from Ethanol, $CO_2$ and Propylene Oxide Using $BWC_{800}$ as Catalyst at 80 Bar $CO_2$ Pressure and 120° C. Temperature Propylene oxide (10.17 gm, 0.175 mol), ethanol (64.70 gm, 1.40 mol) and wood ash catalyst $BWC_{800}$ (7.0 gm, 10% wt/wt) were charged in to 700 ml autoclave vessel. The autoclave vessel was pressurised with $CO_2$ pressure, heated to reach 120° C. temperature and 80 bar pressure under constant stirring during the reaction for 24 hours. Reaction mixture work up was carried out as described in example 3.

Analytical analysis of ethanol fraction reveals that formation of DEC is 5.08 gm (43.05 mmol). The calculated yield of DEC corresponding to propylene oxide is 24.54%.

Example 7

Synthesis of DEC from Ethanol, $CO_2$ and Propylene Oxide Using 5 wt % $BWC_{800}$ as Catalyst In a 700 ml autoclave vessel added propylene oxide (10.17 gm, 0.175 mol), ethanol (64.70 gm, 1.40 mol) and wood ash catalyst $BWC_{800}$ (3.5 gm, 5% wt/wt). The autoclave vessel was pressurised with $CO_2$ pressure, heated to reach 150° C. temperature and 80 bar pressure under constant stirring during the reaction for 24 hours. Reaction mixture work up was carried out as described in example 3.

Analytical analysis of Ethanol fraction had DEC of 5.49 gm (54.86 mmol). The formation yield of DEC with respect to propylene oxide is 26.52%.

Example 8

Synthesis of DEC from Ethanol, $CO_2$ and Propylene Oxide Using 15 wt % $BWC_{800}$ as Catalyst Propylene oxide (10.17 gm, 0.175 mol), ethanol (64.70 gm, 1.40 mol) and wood ash catalyst $BWC_{800}$ (10.5 gm, 15% wt/wt) were charged in to 700 ml autoclave vessel. The autoclave vessel was pressurised with $CO_2$ pressure, heated to reach 150° C. temperature and 80 bar pressure under constant stirring during the reaction for 24 hours. Reaction mixture work up was carried out as described in example 3.

The analytical analysis of ethanol fraction revealed that formation of DEC is 5.27 gm (44.66 mmol). The calculated yield of DEC corresponding to propylene oxide is 25.45%.

Example 9

Synthesis of DEC from Ethanol, $CO_2$ and Propylene Oxide Using 10 wt % of Recovered $BWC_{800}$ from Example 3 as Catalyst Propylene oxide (10.17 gm, 0.175 mol), ethanol (64.70 gm, 1.40 mol) and wood ash recovered catalyst $BWC_{800}$ from example 3 (10.5 gm, 15% wt/wt) were charged into 700 ml autoclave vessel. The autoclave vessel was pressurised with $CO_2$ pressure, heated to reach 150° C. temperature and 80 bar pressure under constant stirring during the reaction for 24 hours. Reaction mixture work up was carried out as described in example 3.

The analytical analysis of ethanol fraction reveals that formation of DEC is 9.85 gm (83.50 mmol). The measured yield of DEC from propylene oxide is 47.6%.

Example 9 shows the recovered catalyst used second time for the monitoring DEC synthesis under standardised reaction conditions. The DEC yield with second time recovered catalyst is slightly lower 47.6% than the previous results. Third cycle usage of wood ash catalyst gave 46.5% of DEC yield.

Example 10

Synthesis of DEC from Ethanol, $CO_2$ and Propylene Oxide Using $BWC_{800}$ as Catalyst at 80 Bar $CO_2$ Pressure and 180° C. Temperature In a 700 ml autoclave, propylene oxide (10.17 gm, 0.175 mol), ethanol (64.70 gm, 1.40 mol) and wood ash catalyst $BWC_{800}$ (7.0 gm, 10% wt/wt) was charged. The autoclave vessel was pressurised with $CO_2$ pressure, heated to 180° C. temperature and 80 bar pressure under constant stirring for reaction time 24 hours. Reaction mixture work up was carried out as described in example 3.

The analytical analysis of ethanol fraction reveals the formation of DEC is 9.86 gm (83.56 mmol). The calculated yield of DEC corresponding to propylene oxide is 47.86%.

Example 11

Synthesis of DEC from Ethanol, $CO_2$ and Ethylene Oxide Using $BWC_{800}$ as Catalyst at 80 Bar $CO_2$ Pressure and 150° C. Temperature 700 ml autoclave was charged with ethylene oxide (7.7 gm, 0.175 mol), ethanol (64.70 gm, 1.40 mol) and wood ash catalyst $BWC_{800}$ (7.0 gm, 10% wt/wt). The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of ethanol fraction reveals that formation of diethyl carbonate is 10.33 gm (87.54 mmol). The calculated yield of diethyl carbonate from ethylene oxide is measured as 50.07%.

Example 12

Synthesis of DMC from Methanol, $CO_2$ and Ethylene Oxide Using $BWC_{800}$ as Catalyst at 80 Bar $CO_2$ Pressure and 150° C. Temperature Ethylene oxide (7.7 gm, 0.175 mol), methanol (44.80 gm, 1.40 mol) and wood ash catalyst $BWC_{800}$ (5.5 gm, 10% wt/wt) were taken in to 700 ml autoclave vessel and closed tightly. The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of methanol fraction reveals that formation of dimethyl carbonate is 8.20 gm (91.11 mmol). The calculated yield of dimethyl carbonate from ethylene oxide is measured as 52.13%.

Example 13

Synthesis of DEC from Ethanol, $CO_2$ and 1,2-Epoxyhexane Using $BWC_{800}$ as Catalyst at 80 Bar $CO_2$ Pressure and 150° C. Temperature The reactants mixture of 1,2-epoxyhexane (17.53 gm, 0.175 mol), ethanol (64.70 gm, 1.40 mol) and wood ash catalyst $BWC_{800}$ (8.25 gm, 10% wt/wt) was charged into autoclave vessel and lid was closed. The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of ethanol fraction reveals that formation of diethyl carbonate is 4.35 gm (36.86 mmol). The calculated yield of diethyl carbonate from epoxyhexane is measured as 21%.

Example 14

Synthesis of DMC from Methanol, $CO_2$ and 1,2-Epoxyhexane Using $BWC_{800}$ as Catalyst at 80 Bar $CO_2$ Pressure and 150° C. Temperature 1,2-epoxyhexane (17.53 gm, 0.175 mol), methanol (44.80 gm, 1.40 mol) and wood ash catalyst $BWC_{800}$ (6.23 gm, 10% wt/wt) were charged into 700 ml autoclave vessel and tightly closed. The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of methanol fraction reveals that formation of dimethyl carbonate is 4.42 gm (49.00 mmol). The calculated yield of dimethyl carbonate from epoxyhexane is measured as 28.06%.

Example 15

Synthesis of Dicyclohexyl Carbonate from Cyclohexanol, $CO_2$ and 1,2-Epoxyhexane Using $BWC_{800}$ as Catalyst at 80 Bar $CO_2$ Pressure and 150° C. Temperature 700 ml autoclave was charged with 1,2-epoxyhexane (17.53 gm, 0.175 mol), cyclohexanol (140.81 gm, 1.40 mol) and wood ash catalyst $BWC_{800}$ (15.8 gm, 10% wt/wt). The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of reaction mixture reveals that formation of dicyclohexyl carbonate is 7.16 gm (31.54 mmol). The calculated yield of dicyclohexyl carbonate from epoxyhexane is measured as 18%.

Example 16

Synthesis of DMC from Methanol, $CO_2$ and Propylene Oxide Using $BWC_{800}$ as Catalyst at 80 Bar $CO_2$ Pressure and 150° C. Temperature The mixture of propylene oxide (10.17 gm, 0.175 mol), methanol (44.80 gm, 1.40 mol) and wood ash catalyst $BWC_{800}$ (5.5 gm, 10% wt/wt) was taken into 700 ml autoclave vessel and closed with lid. The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of methanol fraction reveals that formation of dimethyl carbonate is 8.05 gm (89.5 mmol). The calculated yield of dimethyl carbonate from propylene oxide is measured as 51.11%.

Example 17

Synthesis of Didecyl Carbonate from n-Decanol, $CO_2$ and Propylene Oxide Using $BWC_{800}$ as Catalyst at 80 Bar $CO_2$ Pressure and 150° C. Temperature 700 ml autoclave was charged with propylene oxide (10.17 gm, 0.175 mol), n-decanol (221.60 gm, 1.40 mol) and wood ash catalyst $BWC_{800}$ (23.0 gm, 10% wt/wt). The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of reaction mixture reveals that formation of didecyl carbonate is 19.80 gm (57.89 mmol). The calculated yield of didecyl carbonate from propylene oxide is measured as 33.0%.

Example 18

Synthesis of Dicyclohexyl Carbonate from Cyclohexanol, $CO_2$ and Propylene Oxide Using $BWC_{800}$ as Catalyst at 80 Bar $CO_2$ Pressure and 150° C. Temperature Propylene oxide (10.17 gm, 0.175 mol), cyclohexanol (140.81 gm, 1.40 mol) and wood ash catalyst $BWC_{800}$ (15.0 gm, 10% wt/wt) were taken into 700 ml autoclave vessel and closed tightly. The autoclave vessel was pressurised with $CO_2$ pressure, heated to reach 150° C. temperature and 80 bar pressure under constant stirring during the reaction for 24 hours. Reaction mixture work up was carried out as described in example 1. The quantitative analysis of reaction mixture reveals that formation of dicyclohexyl carbonate is 9.55 gm (42.0 mmol). The calculated yield of dicyclohexyl carbonate from propylene oxide is measured as 24%.

We claim:

1. A single-pot method for preparing dialkyl carbonate, the method comprising:
    (a) dissolving an alkylene oxide in an aliphatic or cyclic aliphatic alcohol,
    (b) adding a wood ash catalyst,
    (c) adding $CO_2$ gas under pressure and heating the reaction mixture,
    (d) cooling the reaction mixture to about room temperature, and depressurizing to obtain dialkyl carbonate.

2. The method as claimed in claim 1, wherein the reaction mixture is filtered to recover the catalyst.

3. The method of claim 1, wherein the aliphatic or cyclic aliphatic alcohols are $C_1$ to $C_{12}$ aliphatic alcohols and $C_1$ to $C_{12}$ cyclic aliphatic alcohols.

4. The method of claim 2, wherein the aliphatic or cyclic aliphatic alcohol is selected from methanol, ethanol, propanol, butanol, amyl alcohol, hexanol, octanol, cyclohexanol and octahexanol.

5. The method of claim 1 wherein the alkylene oxide is selected from the group comprising ethylene oxide, propylene oxide, 1,2-epoxy butane, 1,2-epoxy pentane and 1,2-epoxy hexane.

6. The method of claim 1 wherein the pressure is about 70-90 bar.

7. The method of claim 1 wherein the heating is carried out at a temperature range of about 100-180° C.

8. The method of claim 2 wherein the filtered catalyst is washed with an aliphatic alcohol and dried at about 120° C. for 24 hours for reuse.

9. The method of claim 8 wherein the aliphatic alcohol is methanol or ethanol.

10. The method as claimed in claim 1, wherein the reaction mixture is filtered to recover the catalyst, wherein the filtered catalyst is washed with an aliphatic alcohol and dried at about 120° C. for 24 hours for reuse, and wherein the catalyst obtained is reused in the process of claim 1.

* * * * *